(12) United States Patent
Rossing et al.

(10) Patent No.: US 7,389,149 B2
(45) Date of Patent: Jun. 17, 2008

(54) CONNECTION STRUCTURES FOR EXTRA-VASCULAR ELECTRODE LEAD BODY

(75) Inventors: Martin A. Rossing, Coon Rapids, MN (US); Stephen L. Bolea, Watertown, MN (US); David W. Mayer, Bloomington, MN (US); Aaron Hjelle, Champlin, MN (US); Thomas P. Crowley, Lino Lakes, MN (US); Eric D. Irwin, Minneapolis, MN (US)

(73) Assignee: CVRX, Inc., Minneapolis, MN (US)

( * ) Notice: Subject to any disclaimer, the term of this patent is extended or adjusted under 35 U.S.C. 154(b) by 137 days.

(21) Appl. No.: 11/168,753

(22) Filed: Jun. 27, 2005

(65) Prior Publication Data

US 2006/0004430 A1 Jan. 5, 2006

Related U.S. Application Data

(60) Provisional application No. 60/584,915, filed on Jun. 30, 2004.

(51) Int. Cl.
*A61N 1/05* (2006.01)

(52) U.S. Cl. ................. 607/116; 607/118; 607/126; 600/377

(58) Field of Classification Search ............... 607/2, 607/39–46, 115–118, 126, 132, 149; 600/373, 600/377, 393
See application file for complete search history.

(56) References Cited

U.S. PATENT DOCUMENTS

| | | | |
|---|---|---|---|
| 3,654,933 A | 4/1972 | Hagfors | |
| 3,774,618 A | 11/1973 | Avery | |
| 4,394,866 A | 7/1983 | Hughes | |
| 4,573,481 A | 3/1986 | Bullara | |
| 4,590,946 A | 5/1986 | Loeb | |
| 4,602,624 A | 7/1986 | Naples et al. | |
| 4,920,979 A | 5/1990 | Bullara | |
| 4,979,511 A * | 12/1990 | Terry, Jr. | 600/377 |
| 5,095,905 A | 3/1992 | Klepinski | |
| 5,129,405 A | 7/1992 | Milijasevic et al. | |
| 5,344,438 A | 9/1994 | Testerman et al. | |
| 5,376,108 A | 12/1994 | Collins et al. | |
| 5,423,763 A | 6/1995 | Helland et al. | |
| 5,531,778 A * | 7/1996 | Maschino et al. | 607/118 |
| 5,603,730 A | 2/1997 | Romkee | |
| 5,682,403 A | 10/1997 | Tu et al. | |
| 5,782,898 A | 7/1998 | Dahl et al. | |

(Continued)

*Primary Examiner*—Kennedy J Schaetzle
(74) *Attorney, Agent, or Firm*—Townsend and Townsend and Crew LLP

(57) ABSTRACT

Connection structures on an extra-vascular electrode lead body improve strain relief and strengthen the transition region where electrical conductors carried by the lead body are joined to individual electrodes at the distal end of the lead. The electrodes include structure or mechanisms for externally securing the electrode assembly to a body part. A first connection structure is located on the lead body proximal the electrodes to anchor the lead body to a first anchor location in the body that generally moves in concert with the body part. A second connection structure is located on the lead body proximal to the first connection structure to anchor the lead body to a second anchor location that is at least partially independent of movement of the body part. The first and second anchor location are offset by a distance that is less than a distance between the first and second connection structures to provide strain relief for the electrodes.

11 Claims, 6 Drawing Sheets

U.S. PATENT DOCUMENTS

| | | |
|---|---|---|
| 5,938,596 A | 8/1999 | Woloszko et al. |
| 6,522,926 B1 | 2/2003 | Kieval et al. |
| 6,600,956 B2 * | 7/2003 | Maschino et al. .......... 607/118 |
| 2003/0060857 A1 | 3/2003 | Perrson et al. |
| 2004/0010303 A1 | 1/2004 | Bolea et al. |

* cited by examiner

CONNECTION STRUCTURES FOR EXTRA-VASCULAR ELECTRODE LEAD BODY

CROSS-REFERENCES TO RELATED APPLICATIONS

The present application claims the benefit of Provisional U.S. Patent Application No. 60/584,915, filed Jun. 30, 2004, the full disclosure of which is incorporated herein by reference.

BACKGROUND OF THE INVENTION

FIELD OF THE INVENTION

This invention relates generally to electrode leads for implantable medical devices. More particularly, the present invention relates to connection structures for anchoring an extra-vascular electrode lead body and providing improved strain relief, as well as providing a more robust region for transitioning electrical conductors carried by the lead body to individual electrodes at the distal end of the lead.

Implantable pulse generator medical devices are well known in the art, and include medical devices such as pacemakers, defibrillators and muscle and nerve stimulators. Generally, these medical electrical devices comprise an implantable pulse generator unit and an electrical lead or leads connected to one or more electrodes. The electrode may be placed adjacent to a particular part of the human body, such as within the myocardial tissue of the heart, within a vein or proximate any other tissue to be stimulated and/or sensed. The electrode, which is attached at the distal end of the lead, is attached to the appropriate location in the human body, and the proximal end of the lead is connected to a header of the implantable pulse generator.

In the case of pacemakers and defibrillators, the vast majority of electrical leads now used with these implantable devices are intra-vascular leads, i.e. endocardial leads or transvenous leads, that are introduced into a vein and then routed through the vein to the right side of the heart. Once in the heart, tines or screw-in structures on the distal end of the lead are generally used to secure the electrodes in position. In the most cases, a suture sleeve that surrounds the lead body of an intra-vascular lead is positioned at a location well proximal to the electrodes where the lead body enters the vein. The suture sleeve includes structure that permits the suture sleeve, and hence, the electrical lead to be sutured to the vein. Examples of various designs for suture sleeves for intra-vascular leads are shown in U.S. Pat. Nos. 5,129, 405, 5,423,763 and 5,603,730. U.S. Pat. No. 5,376,108 describes a dual suture collar technique for an intra-vascular lead that utilizes two suture collars tethered to one another by a-flexible retaining member. Other examples of techniques for securing intra-vascular leads in position are shown in U.S. Pat. Nos. 4,394,866, 5,682,403 and 5,782, 898.

Extra-vascular electrical leads, i.e., leads that are not implanted within a vein or artery, are more commonly used with other forms of implantable tissue stimulators, such as nerve stimulators or tissue stimulators. In the case of nerve stimulators, early designs for nerve stimulation electrical leads secured the electrode around a desired location along a nerve by positioning the electrode in a flexible insulator cuff that was then wrapped around the nerve and sewn together. Examples of this wrapped cuff technique are shown in U.S. Pat. Nos. 3,654,933 and 3,774,618.

While simple in design, chronically reliable electrical connections were difficult to attain with these types of prior art cuffs. In a chronic setting, it was found that many medical electrical leads with such simple cuff arrangements could electrically or mechanically damage a nerve. Mechanically induced damage included thickened epineurium due to accumulation of connective tissue between the electrode and the nerve, increased subperineural and endoneural connective tissue, endoneural edema, demyelinization, axonal degeneration and frank axonal loss. Such damage may be caused in several ways. First, if the lead and the electrode that interfaces with the nerve does not move with the nerve, then abrasion of the nerve may result. Second, the presence of the lead and the electrode may cause edema or swelling of the nerve. As the nerve swells, the nerve may be constricted by the electrode. A compressive force may thereby be induced upon the nerve. Prior art cuff nerve electrodes also could led to electrically induced damage. Such damage results in axonal degeneration as well as nerve edema. While it has been shown that the type of electrical stimulation, e.g., frequency, waveform, and amplitude may be a significant factor, the actual electrode design could also affect the degree of electrically induced damage.

In recognition of these problems, so-called "self sizing" nerve cuff electrodes were developed to avoid such damage. Examples of such self-sizing cuff electrode may be seen in U.S. Pat. Nos. 4,573,481, 4,602,624, 4,920,979, 5,344,438, 5,095,905 and 5,938,596. To date, however, such electrodes have not produced long-term satisfactory results because they can to be difficult to install and because they are more difficult to keep secured in a given location as a result of their self sizing design.

Another example of a nerve electrode arrangement is shown in U.S. Pat. No. 4,590,946 which describes an electrode system that includes two or more electrically conductive elements embedded in a helically wound substrate made of insulative material. A separate membrane pouch is needed to insulate the electrode from adjacent body tissue. This pouch greatly increases the bulk of the electrode and, thus, increases the potential for mechanically induced neural trauma. A strain relief for the lead-in conductors is taught by this patent in the form of a single strap around the conductors that is screwed or otherwise surgically attached to adjacent body tissue.

The lead body of an implantable extra-vascular electrical lead is made of flexible resilient material to accommodate the movement of the nerve bundle itself and the movement of the nerve bundle relative to surrounding tissue. Since the electrode(s) of the electrical lead is attached to the nerve, any relative movement between the nerve bundle and the surrounding tissue can impart a strain on the junction between the lead conductors in the lead body and the electrode, as well as on the nerve itself. Any mechanical forces transmitted to the nerve via the lead conductors can cause damage to the nerve or dislocation of the electrode(s).

One example of a therapy delivered by an implantable pulse generator to a nerve stimulation electrical lead is a baroreflex activation lead and electrode that is positioned at the carotid sinus for baroreflex activation. An intra-vascular electrical lead positioned inside the carotid sinus for this therapeutic application is shown in U.S. Pat. No. 6,522,926. U.S. Publ. Appl. Nos. 2003/0060857A1 and 2004/0010303A describe extra-vascular electrical leads wrapped around the exterior of the carotid sinus in order stimulate the baroreflex activation. While different electrode structures and arrangements for suture pads to secure these extra-vascular electrodes are described in these publications, there is no description or discussion of how to secure the lead body of such extra-vascular electrical leads.

Accordingly, there is a need for a system that overcomes the problems set forth above and contemplates a new and robust connection structure that minimizes the stress on the lead body caused by body motion without straining the electrode.

BRIEF SUMMARY OF THE INVENTION

The present invention provides connection structures for anchoring an extra-vascular electrode lead body that improve strain relief and strengthen the transition region where electrical conductors carried by the lead body are joined to individual electrodes at the distal end of the lead. The extra-vascular electrical lead has an elongated flexible lead body with a connector assembly at a proximal end connected to at least one conductor carried within the lead body that is connected at a distal end to at least one electrode assembly. The electrode assembly includes structure or mechanisms for externally securing the electrode assembly to a body part. A distal connection structure is located on the lead body proximal the electrode assembly to anchor the lead body to a distal anchor location in the body that generally moves in concert with the body part. A proximal connection structure is located on the lead body proximal to the distal connection structure to anchor the lead body to a proximal anchor location in the body that is at least partially independent of movement of the body part. The distal anchor location and the proximal anchor location are offset in the body by a distance that is less than a distance between the distal and proximal connection structures in order to provide strain relief for the electrode assembly against movement of the body part.

In a preferred embodiment, the electrical lead is connected at a proximal end to a pulse generator implanted in the pectoral region of the patient. The electrode assembly at the distal end of the lead is attached to the carotid sinus. The carotid sinus may move when the patient swallows or has other small movements in the head. Therefore, it is desirable to relieve strain between the electrode on the carotid sinus and a distal fixation point associated with the distal connection structure. This distal fixation point moves in concert with the carotid sinus to prevent strain from being applied directly to the carotid sinus. A proximal fixation point is also provided at the proximal connection structure. The proximal fixation point provides strain relief for larger movements of a patient's head or neck. The lead body between the distal and proximal fixation points are optimally, but not necessarily, formed in the shape of a loop.

DETAILED DESCRIPTION OF THE INVENTION

Figure 1:
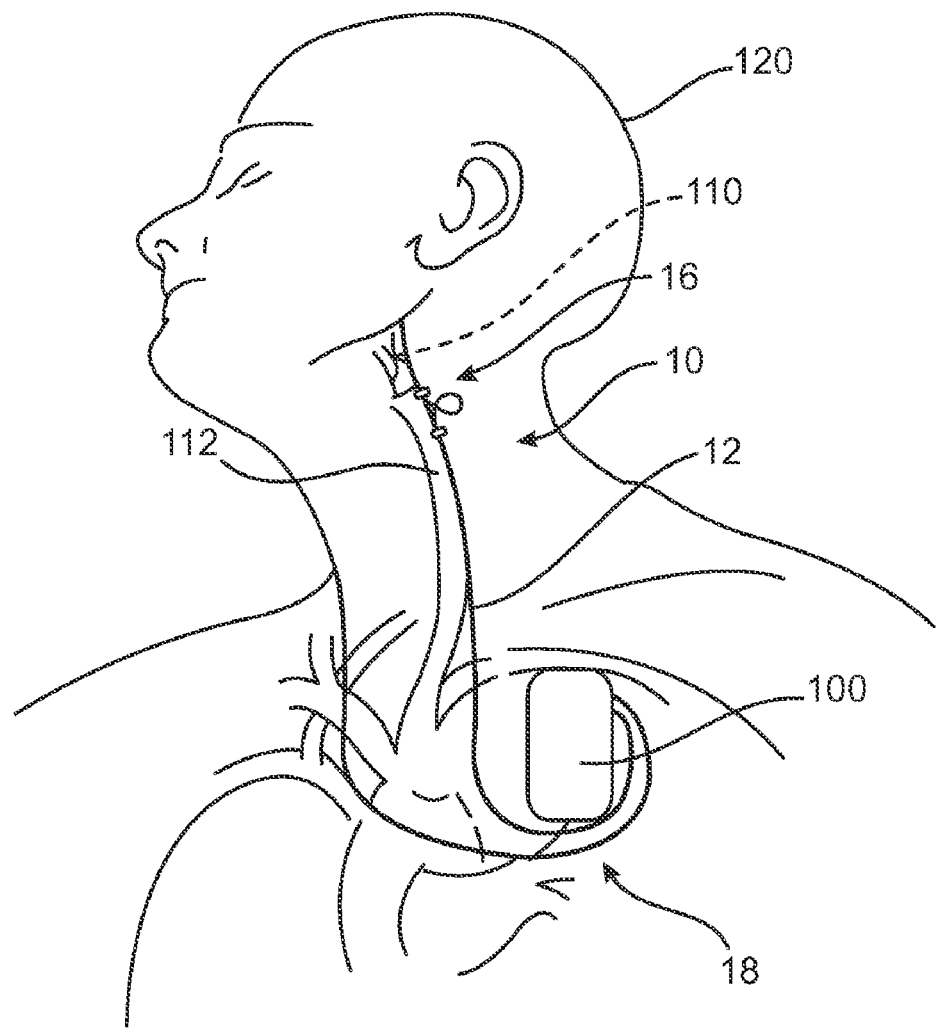
FIG. 1 is a partially exposed view of an extra-vascular lead implanted in accordance with a preferred embodiment and connected to an implantable pulse generator.

Referring to FIGS. 1 through 5 an extra-vascular electrode lead 10 will be described that improves strain relief and strengthens a transition or junction region 14 where electrical conductors 22, 24 (FIG. 5) carried by an elongated flexible lead body 12 are joined to individual electrodes 32, 34, 36 at the distal end 16 of the lead 10. The elongated flexible lead body 12 is made of an insulator material with a connector assembly 21 (FIG. 3) at a proximal end 18 of the lead body 12. In a preferred embodiment, the connector assembly 21 is connected to a pair of conductors 22, 24 (FIG. 25) carried within the lead body 12 that are connected at their distal ends to an electrode assembly 30. The electrode assembly 30 includes structure or mechanisms, such as electrode tips 38, for externally securing the electrode assembly 30 to a body part. A distal connection structure 50 is located on the lead body 12 proximal the electrode assembly 30 to anchor the lead body 12 to a distal anchor location 52 in the body that generally moves in concert with the body part to which the electrode assembly 30 is secured. A proximal connection structure 60 is located on the lead body 12 proximal to the distal connection structure 50 to anchor the lead body 12 to a proximal anchor location 62 in the body that is at least partially independent of movement of the body part to which the electrode assembly 30 is secured. The lead 10 is implanted such that the distal anchor location 52 and the proximal anchor location 62 are offset in the body by a distance C (FIG. 2) that is less than a distance B (FIG. 3) between the distal connection structure 50 and the proximal connection structure 60 in order to provide strain relief for the electrode assembly 30 against movement of the body part.

The connector assembly 21 (FIG. 3) at the proximal end 18 of lead body 12 is connected to an implantable pulse generator 100 (FIG. 1). The pulse generator 100 is commonly implanted in the pectoral region of the patient. Although the preferred embodiment of the present invention will be described with respect to an implantable baroreflex activation electrode that activates the baroreflex at the carotid sinus, it will be understood that the extra-vascular lead 10 in accordance with the present invention can be used for any number of applications of tissue, nerve or organ stimulation in the body. While the preferred embodiment will be described with respect to a baroreflex activation at the carotid sinus alone, it will also be recognized that the present invention can be utilized as part of a combination device featuring, for example, both cardiac sensing/stimulation via intra-vascular electrical leads, as well as other tissue stimulation by extra-vascular leads 10 in accordance with the present invention. The apparatus may be used any time a lead is implanted in tissue (nerves, muscles, vasculars) that may move independently in the body. For a more detailed description of the operation and arrangement of the preferred embodiment of a nerve stimulation electrical lead 10 for the carotid sinus, reference is made to U.S. Publ. Appl. Nos. 2003/0060857A1 and 2004/0010303A which describe extra-vascular electrical leads wrapped around the exterior of the carotid sinus in order stimulate the baroreflex activation, the disclosure of each of which is hereby incorporated by reference.

Figure 2:
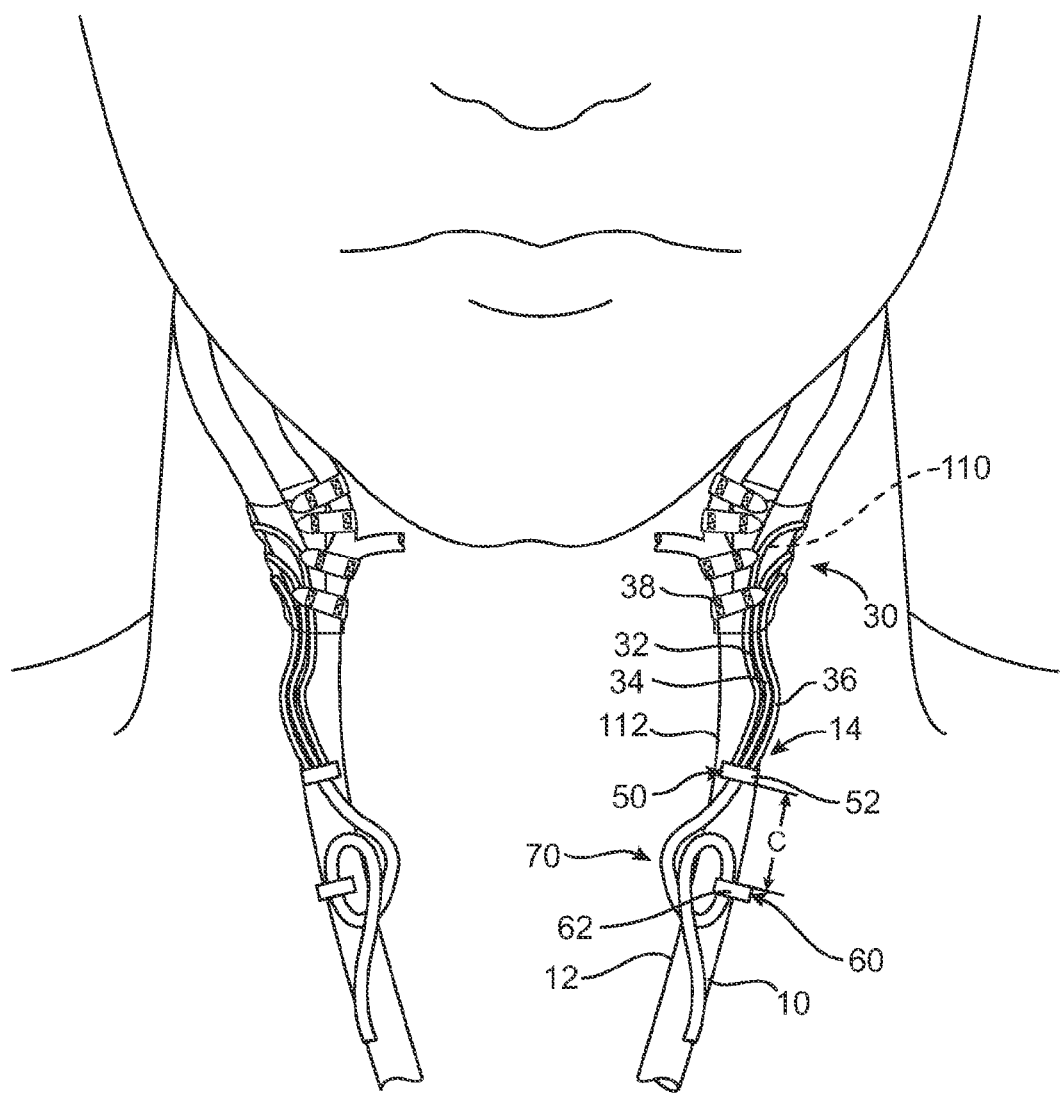
FIG. 2 is a detailed view of an electrode assembly of FIG. 1 shown secured in position on the carotid artery.

As shown in FIGS. 1 and 2 the carotid sinus 110 and carotid artery 112 may move when the patient swallows or moves his or her head 120. The extra-vascular lead 10 of the present invention has been designed to provide a strain relief between the electrode coils 32, 34, and 36 on the carotid sinus 110 at a distal fixation point 52. This distal fixation point 52 preferably is along the artery adventitia or periadventitia that moves in concert with the carotid sinus 110 to, prevent strain from being applied directly to the carotid sinus 110. In the preferred embodiment, the proximal fixation point 62 is located proximal to the distal fixation point along the carotid sheath or adjacent tissue. Proximal fixation point 62 provides strain relief for relatively larger movement of a patient's head 120 and enables a loop 70 of the lead body 12 to become larger or smaller as the distance between distal fixation point 52 and proximal fixation point 62 varies.

Figure 3:
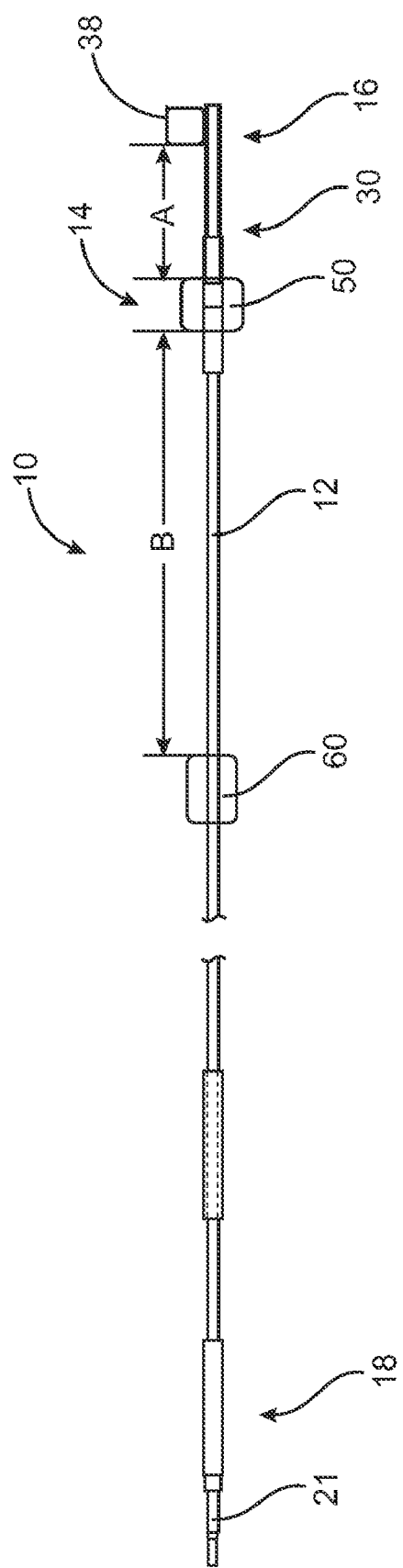
FIG. 3 is a front view of the extra-vascular lead incorporating the present invention.
Figure 4:
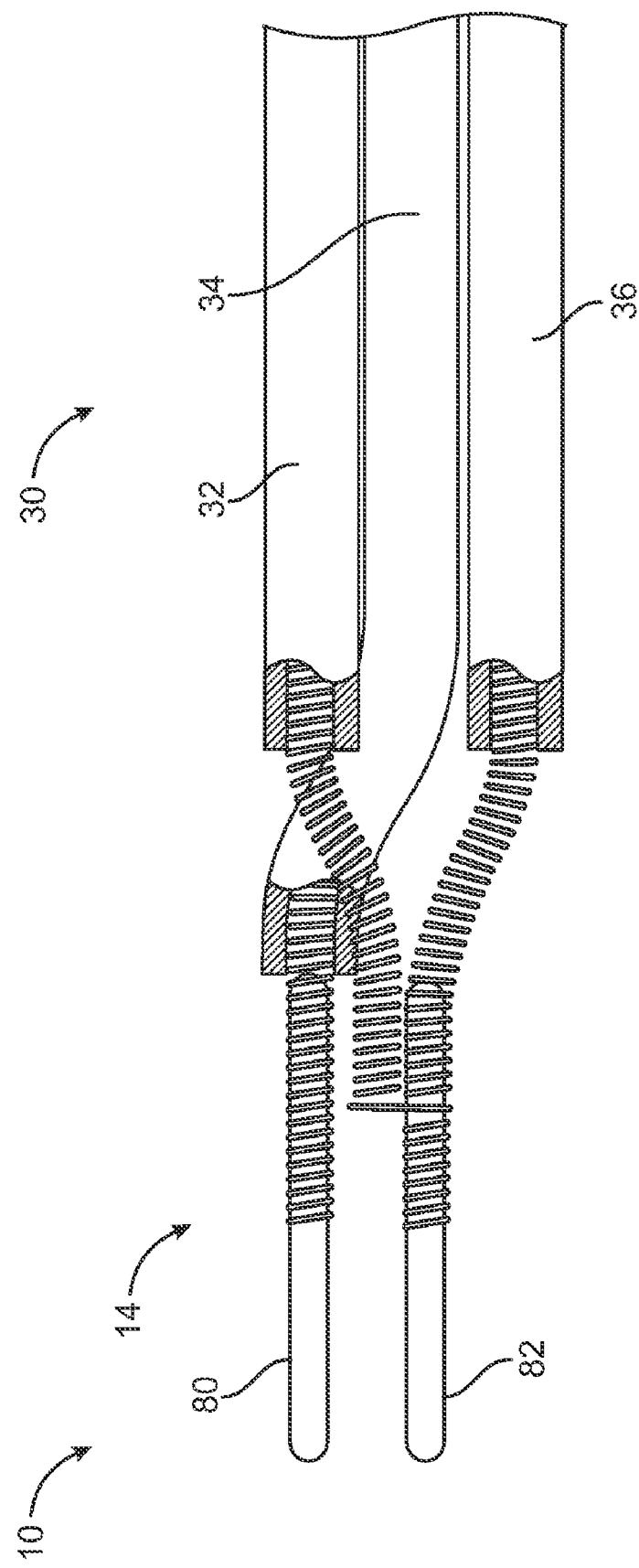
FIGS. 4 and 5 are partially exposed views showing the details of the configuration of the junction region between the electrode assembly and the lead body.
Figure 5:
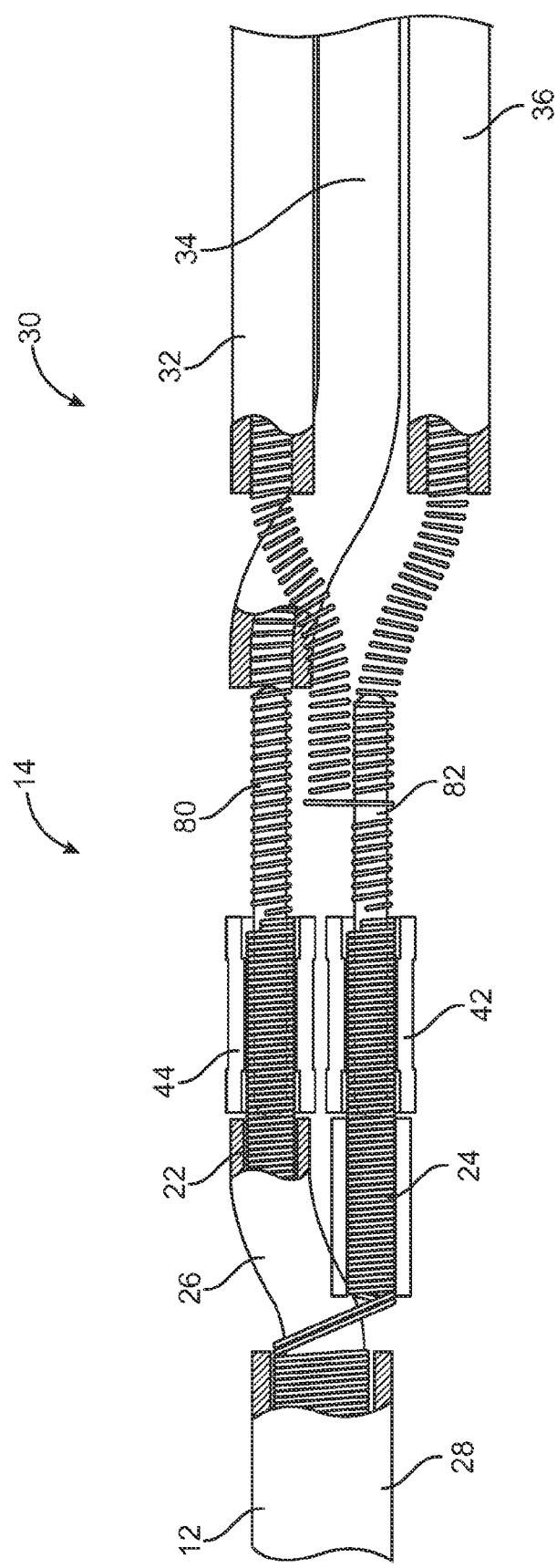

With reference to FIGS. 4 and 5, a view of the details of the junction or transition region 14 of the lead 10 is shown. In the preferred embodiment, electrode assembly 30 includes an outer electrode coil 32, center electrode coil 34, and, outer electrode coil 36. Coils 32, 34, and 36 are preferably helically-shaped and at least partially covered by an insulator. Coils 32, 34, and 36 have a proximal end and a distal end opposite the proximal end. The proximal end of each of the coils 32, 34, and 36 include a plurality of electrode tips 38 (FIG. 3). The electrode tips 38 serve as contact elements and in the preferred embodiment are attached to the carotid sinus nerve 110 (FIG. 1), although tips 38 may be attached to a variety of structures including other nerves, arteries, veins, organs, or tissues while remaining within the scope of the present invention.

Coils 32, 34, and 36 are fabricated of a conductive material. In a preferred embodiment, coils 32, 34, and 36 are: fabricated from a platinum/iridium alloy. A proximal end of coil 34 is shown attached to pin 80, while ends of coils 32, and 36 are shown attached to pin 82 (IFIGS. 4 and 5). This configuration enables three coils 32, 34, and 36 to be connected into two conductors 22,24 via the pins 80, 82.

In a preferred embodiment, the proximal end of center coil 34 is welded to pin 80. Proximal ends of the coils of electrodes 32 and 36 are welded to pin 82. Most preferably, there are at least three free turns of the coils 32 and 36 between the end of the pin 82 and the first weld. Likewise, there are at least three free turns of the electrode coils 34 between the end of the pin 80 and the first weld. This configuration provides robust weld adhesion by the respective electrode coils 32, 34, and 36.

The interaction of pins 80 and 82 with lead body conductors 22, 24 at junction region 14 is shown in FIG. 5. Pin 82 is inserted into a housing 42 and pin 80 is inserted into a housing 44 such that pin 82 touches conductor 24 and pin 82 touches conductor 22. In a preferred embodiment, housings 42 and 44 are crimped to apply pressure of housings 42 and 44 against pins 82 and 80, respectively.

Conductor 22 enters the interior of lead body 12 and is surrounded by insulator 26. Conductor 24 enters lead body 12 and is disposed around the exterior of insulator 26. Insulator 28 is disposed about the exterior of conductor 24, and effectively isolates lead body 12 from the exterior environment. In this configuration, insulator 26 also serves to isolate conductor 24 from conductor 22 while combining the two lead conductors 22 and 24 into one compact coil within the lead body 12. Conductors 22, 24 are preferably fabricated from a Cobalt-35 Nickel-20 Chromium-10 Molybdenum alloy with a silver core, although a variety of materials may be used while remaining within the scope of the invention.

Figure 6:
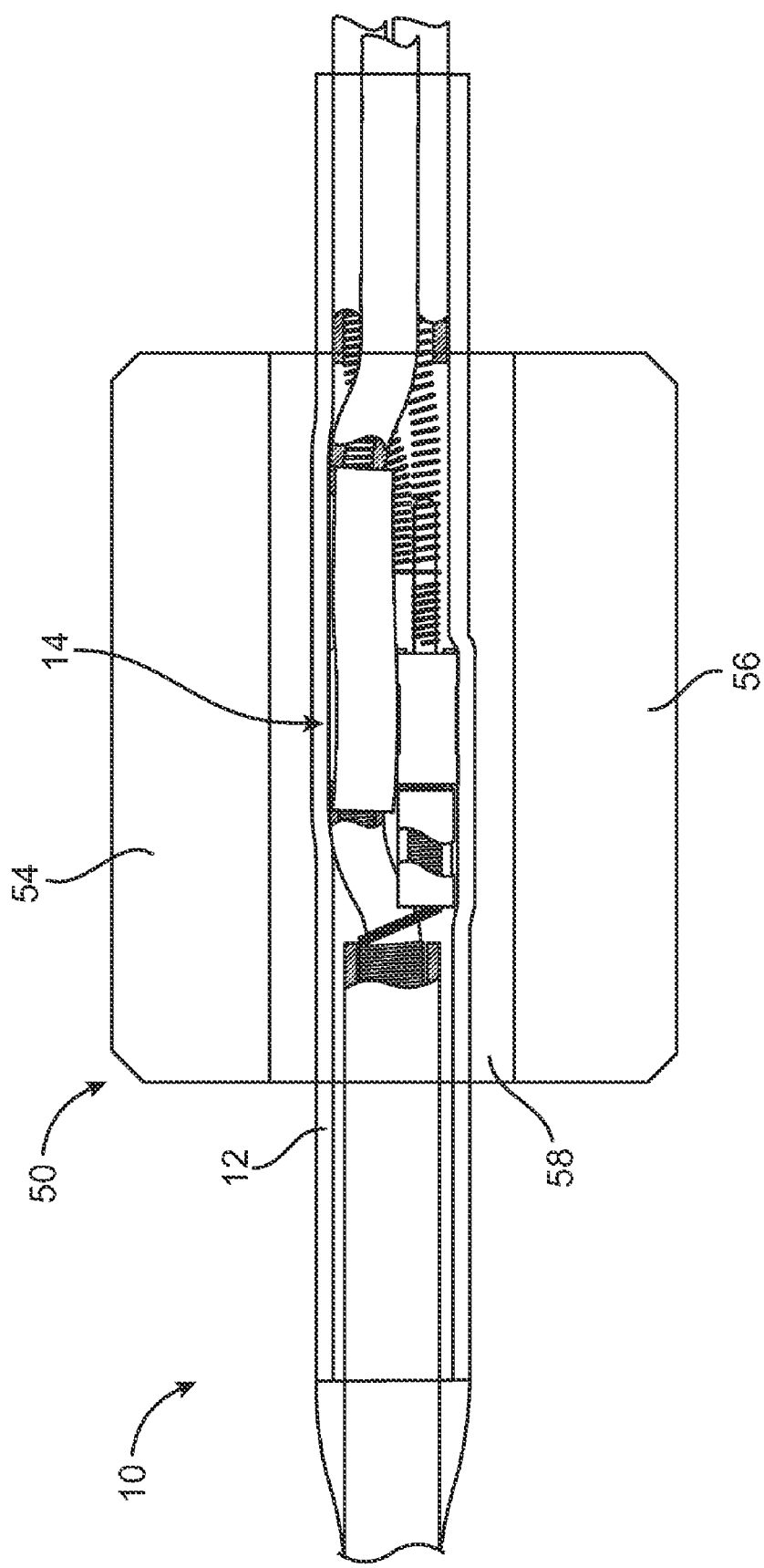
FIG. 6 is a side view showing the electrode-main body junction of the connection apparatus incorporating the present invention.

In FIG. 6, the distal connection structure 50 is shown in the preferred embodiment in the form of a first suture pad. First suture pad 50 is attached at fixation point 52 as shown in FIG. 2. Suture pad 50 comprises dual suture wings 54, 56 and body 58. Body 58 joins dual suture wings 54 and 56 and surrounds junction 14 while providing strain relief for the electrical lead 10. In another configuration, body 58 is attached to the exterior of the lead body 12 at junction 14.

In the preferred embodiment, the proximal connection structure 60 is shown in the form of a second suture pad 60 (FIGS. 2 and 3). Second suture pad 60 is attached at proximal fixation point 62. Suture pad 60 is similar in configuration to suture pad 50 and also includes dual suture wings 64 and 66 that form a strain relief. Suture pad 60 is attached to, or disposed about the exterior of lead body 12.

Although the preferred embodiment of the connection structures 50, 60 have been described in terms of a suture pad, it will be recognized that other forms of surgical connection structures and mechanisms may be used to secure the lead body 12 at the locations 52, 62. Examples of such other forms of surgical connection structures and mechanisms would include anchoring or suture sleeves or similar expansions or bulges of the insulative material of the lead body to permit more effective suturing, clasps, snaps or fasteners, hook and latch mechanisms, or adhesive pads or structures.

With reference to FIG. 2, selective placement of the distal and proximal connection structures 50 and 60 at anchor locations 52 and 62 takes up the stress on the lead body 12 caused by body motion without straining the electrode coils 32, 34, and 36. Placement of the connection structures allows the physician to create a strain relief loop 70 that allows the forces from the body to be absorbed by the loop 70 in lead body 12 rather than the sutures on the electrode tips 38 or suture wings 50 or 60.

The design of the present invention is intended to leave slack in between the two anchor locations 52, 62 to prevent strain on one fixation point from being transferred longitudinally to the other fixation point. The slack is optimally, but not required to be, in the shape of an overlapping loop formed of the lead body 12. Strain on one fixation point is thus taken up by the slack in the lead body 12, rather than being transferring to the other independent fixation point. The arrangement in the form of an overlapping loop also orients the strain in a more longitudinal direction, rather than a direction transverse to the lead body as the portion of the lead body adjacent the fixation points is oriented more longitudinally going into the loop, rather than having an immediate curve if the lead body were to be positioned in the form of a non-overlapping omega-shaped hoop. FIGS. 2 and 3 show the preferred ranges of distances for locating the distal and proximal connection structures 50, 60 and the distal and proximal locations 52, 62. Distance A between electrode tips 38 and distal connection structure 50 is at 0.5 cm, preferably being in the range from 1.0 cm to 5.0 cm. Similarly, the distance B between the suture pad 50 and suture pad 60 is between at least 2.5 cm, preferably being in the range from 5.0 cm to 18.0 cm.

It is to be understood that variations in the present invention can be made without departing from the novel aspects of this invention as defined in the claims.

What is claimed is:

1. An extra-vascular lead for use with an implantable medical device, said lead comprising:
   an elongated flexible lead body having a proximal end and a distal end and two conductors extending therebetween;
   a connector disposed on the proximal end of the lead body and adapted to electrically and mechanically attach to the implantable medical device;
   at least three electrodes electrically connected to the two conductors at the distal end of the leady body;

a proximal connection structure adapted to anchor the lead body at a proximal location on a patient body structure; and a distal connection structure adapted to anchor the lead body to a distal location on the patient body structure;

wherein the one conductor is attached to one electrode and the other conductor is attached to the other two electrodes, as part of the distal connection structure;

wherein the electrodes comprise electrode coils and the two conductors comprise coiled wires and wherein a pin is inserted into adjacent ends of an electrode coil and a coiled wire to join a conductor to one or two electrodes.

2. The extra-vascular electrical lead of claim 1 wherein a first electrode coil and a second electrode coil are each wound around a first pin at least two times and a third electrode coil is wrapped around a second pin at least two times.

3. An extra-vascular lead for use with an implantable medical device, said lead comprising:

an elongated flexible lead body having a proximal end and a distal end and two conductors extending therebetween;

a connector disposed on the proximal end of the lead body and adapted to electrically and mechanically attach to the implantable medical device;

at least three electrodes electrically connected to the two conductors at the distal end of the leady body;

a proximal connection structure adapted to anchor the lead body at a proximal location on a patient body structure; and a distal connection structure adapted to anchor the lead body to a distal location on the patient body structure;

wherein the one conductor is attached to one electrode and the other conductor is attached to the other two electrodes, as part of the distal connection structure;

wherein the electrodes comprise electrode coils of a fine wire and the conductors comprise a thicker wire thicker than the fine wire.

4. The extra-vascular electrical lead of claim 3 wherein the electrode coils have-an inner diameter of less than about 0.02 inches and the conductors have an inner diameter of greater than about 0.02 inches.

5. A method of implanting an extra-vascular electrical lead for use with an implantable medical device to electrically stimulate and/or sense a body part, the method comprising:

providing an extra-vascular electrical lead comprising:

an elongated flexible lead body having a proximal end and a distal end and two conductors extending therebetween;

a connector disposed on the proximal end of the lead body and adapted to electrically and mechanically attach to the implantable medical device;

at least three electrodes electrically connected to the two conductors at the distal end of the leady body;

a proximal connection structure adapted to anchor the lead body at a proximal location on a patient body structure; and a distal connection structure adapted to anchor the lead body to a distal location on the patient body structure; and electrode tips for anchoring a proximal end of the electrodes to the body structure, wherein the electrode tips are separated from the distal connection structure by a distance of at least 0.5 cm, wherein the one conductor is attached to one electrode and the other conductor is attached to the other two electrodes, as part of the distal connection structure, wherein the proximal and distal connection structures are separated by a distance of at least 2.5 cm;

securing the at least three electrodes externally to the body part at an electrode attachment location;

anchoring the distal connection structure to a distal anchor location in the body that generally moves in concert with the body part, the distal anchor location being at a first distance which is greater than the distance from the location of a proximal-most electrode to the location of the distal connection structure;

anchoring the proximal connection structure to aproximal anchor location in the body that is at least partially independent of movement of the body part, the proximal connection structure being located at a second distance along the lead from the distal connection structure and the proximal anchor location being selected such that the distal anchor location and the proximal anchor location are offset in the body by a third distance that is less than the second distance such that the distal and proximal connection structures provide strain relief for the electrode against movement of the body part; and operably connecting the connector to the implantable medical device.

6. The method of claim 5 wherein the first distance is in the range from 1.0 cm to 5.0 cm and the second distance is in the range from 5.0 cm to 18.0 cm.

7. The method of claim 5 wherein the body part is the carotid sinus and the distal anchor location is along the artery adventitia or periadventitia and the second proximal anchor location is along the carotid sheath or adjacent tissue.

8. The method of claim 5 wherein the first distance is in the range from 2.0 cm to 3.0 cm and the second distance is in the range from 7.5 cm to 12.5 cm and the proximal anchor location is along the carotid sheath or adjacent tissue.

9. The method of claim 5 further comprising:

creating an overlapping loop of the lead between the distal and the proximal anchor locations prior to anchoring the proximal connection structure.

10. An extra-vascular lead for use with an implantable medical device, said lead comprising:

an elongated flexible lead body having a proximal end and a distal end and two conductors extending therebetween;

a connector disposed on the proximal end of the lead body and adapted to electrically and mechanically attach to the implantable medical device;

at least three electrodes electrically connected to the two conductors at the distal end of the leady body;

a proximal connection structure adapted to anchor the lead body at a proximal location on a patient body structure; and a distal connection structure adapted to anchor the lead body to a distal location on the patient body structure;

electrode tips for anchoring a proximal end of the electrodes to the body structure, wherein the electrode tips are separated from the distal connection structure by a distance of at least 0.5 cm; and wherein one conductor is attached to one electrode and the other conductor is attached to the other two electrodes, as part of the distal connection structure;

wherein the proximal and distal connection structures are separated by a distance of at least 2.5 cm.

11. A method of implanting an extra-vascular electrical lead for use with an implantable medical device to electrically stimulate and/or sense a body part, the method comprising:

provffding an extra-vascular electrical lead comprising:

an elongated flexible lead body having a proximal end and a distal end and two conductors extending therebetween;

a connector disposed on the proximal end of the lead body and adapted to electrically and mechanically attach to the implantable medical device;

at least three electrodes electrically connected to the two conductors at the distal end of the leady body;

a proximal connection structure adapted to anchor the lead body at a proximal location on a patient body structure;

a distal connection structure adapted to anchor the lead body to a distal location on the patient body structure; and electrode tips for anchoring a proximal end of the electrodes to the body structure, wherein the electrode tips are separated from the distal connection structure by a distance of at least 0.5 cm, wherein the one conductor is attached to one electrode and the other conductor is attached to the other two electrodes, as part of the distal connection structure, wherein the proximal and distal connection structures are separated by a distance of at least 2.5 cm;

providing instructions for implanting the lead, comprising;

securing the at least three electrodes externally to the body part at an electrode attachment location;

anchoring the distal connection structure to a distal anchor location in the body that generally moves in concert with the body part, the distal anchor location being at a first distance which is greater than the distance from the proximal-most electrode attachment location. to the distal connection structure;

anchoring the proximal connection structure to a proximal anchor location in the body that is at least partially independent of movement of the body part, the proximal connection structure being located at a second distance along the lead from the distal connection structure and the proximal anchor location being selected such that the distal anchor location and the proximal anchor location are offset in the body by a third distance that is less than the second distance such that the distal and proximal connection structures provide strain relief for the electrode against movement of the body part; and operably connecting the connector to the implantable medical device.

* * * * *